United States Patent
Nakazato et al.

(10) Patent No.: US 8,106,194 B2
(45) Date of Patent: Jan. 31, 2012

(54) PYRROLOPYRIMIDINE AND PYRROLOTRIAZINE DERIVATIVES

(75) Inventors: Atsuro Nakazato, Tokyo (JP); Taketoshi Okubo, Tokyo (JP); Dai Nozawa, Tokyo (JP); Tomoko Tamita, Tokyo (JP); Ludo E. J. Kennis, Beerse (BE)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 1545 days.

(21) Appl. No.: 10/584,946

(22) PCT Filed: Jan. 6, 2005

(86) PCT No.: PCT/JP2005/000319
§ 371 (c)(1),
(2), (4) Date: Jul. 5, 2006

(87) PCT Pub. No.: WO2005/066142
PCT Pub. Date: Jul. 21, 2005

(65) Prior Publication Data
US 2011/0137031 A1 Jun. 9, 2011

(30) Foreign Application Priority Data
Jan. 6, 2004 (JP) .................................. 2004-001311

(51) Int. Cl.
C07D 251/02 (2006.01)
C07D 251/42 (2006.01)
C07D 239/70 (2006.01)

(52) U.S. Cl. ........................................ 544/211; 544/282

(58) Field of Classification Search .................. None
See application file for complete search history.

(56) References Cited

U.S. PATENT DOCUMENTS

| | | |
|---|---|---|
| 6,187,781 B1 | 2/2001 | Nakazato et al. |
| 6,600,038 B1 | 7/2003 | Nakazato et al. |
| 6,852,732 B2 | 2/2005 | Nakazato et al. |
| 2005/0209253 A1 | 9/2005 | Nakazato et al. |
| 2007/0060602 A1 | 3/2007 | Nakazato et al. |
| 2007/0254898 A1 | 11/2007 | Nakazato et al. |
| 2007/0270588 A1 | 11/2007 | Bischoff et al. |
| 2007/0293670 A1 | 12/2007 | Nakazato et al. |

FOREIGN PATENT DOCUMENTS

| | | |
|---|---|---|
| EP | 0 729 758 A2 | 9/1996 |
| WO | 94/13676 A1 | 6/1994 |
| WO | 97/29110 A1 | 7/1997 |
| WO | WO 98/42699 A1 | 1/1998 |
| WO | WO 98/08847 A1 | 3/1998 |
| WO | WO 98/35967 A2 | 8/1998 |
| WO | 98/47903 A1 | 10/1998 |
| WO | 99/51597 A1 | 10/1999 |
| WO | 99/51599 A1 | 10/1999 |
| WO | 99/51600 A1 | 10/1999 |
| WO | WO 00/53604 A1 | 9/2000 |
| WO | WO 02/02549 A1 | 1/2002 |
| WO | WO 2004/058767 A1 | 7/2004 |
| WO | WO 2005/066142 A3 | 7/2005 |
| WO | WO 2005/066178 A1 | 7/2005 |
| WO | WO 2005/066182 A1 | 7/2005 |
| WO | WO 2005/085253 A1 | 9/2005 |
| WO | WO 2006/001501 A1 | 1/2006 |
| WO | WO 2006/001511 A1 | 1/2006 |

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
Mario Bonamico et al., "Condensation Reactions of Tetracyanoethylene and its Monoanion Promoted by Lewis Acids: Synthesis and Crystal, Moleuclar, and Electronic Structure of a Novel Heterocycle, the 2, 3, 6, 7-Tetracyano-5-(tricyanoethenylimino)-3H-1,4,7b-triazabenzo[i,j]pentalenide Ion", J. Chem. Soc. Perkin Trans. 2, 121-125 (1990).
Sudha R. Vippagunta, et al., "Crystalline Solids", Advanced Drug Delivery Reviews, vol. 48. pp. 3-26, 2001.
Sudha R. Vippagunta et al., "Crystalline Solids", Advanced Drug Delivery Reviews, vol. 48, pp. 3-26, 2001.

* cited by examiner

Primary Examiner — Jeffrey Murray
(74) Attorney, Agent, or Firm — Sughrue Mion, PLLC

(57) ABSTRACT

An object of the present invention is to provide an antagonist against CRF receptors which is effective as a therapeutic or prophylactic agent for diseases in which CRF is considered to be involved, such as depression, anxiety, Alzheimer's disease, Parkinson's disease, Huntington's chorea, eating disorder, hypertension, gastral diseases, drug dependence, epilepsy, cerebral infarction, cerebral ischemia, cerebral edema, cephalic external wound, inflammation, immunity-related diseases, alpecia, irritable bowel syndrome, sleep disorders, dermatitides, schizophrenia, pain, etc. A pyrrolopyrimidine or pyrrolotriazine derivative substituted with a carbamoyl group represented by the following formula [I]: has a high affinity for CRF receptors and is effective against diseases in which CRF is considered to be involved.

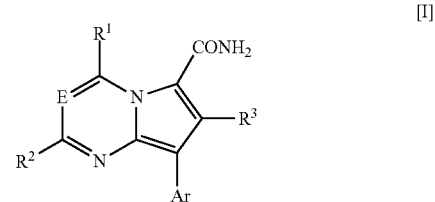

7 Claims, No Drawings

PYRROLOPYRIMIDINE AND PYRROLOTRIAZINE DERIVATIVES

This Application is a 371 of PCT/JP2005/000319, filed Jan. 6, 2005.

DETAILED DESCRIPTION OF THE INVENTION

1. Technical Field

The present invention relates to a therapeutic agent for diseases in which corticotropin releasing factor (CRF) is considered to be involved, such as depression, anxiety, Alzheimer's disease, Parkinson's disease, Huntington's chorea, eating disorder, hypertension, gastral diseases, drug dependence, cerebral infarction, cerebral ischemia, cerebral edema, cephalic external wound, inflammation, immunity-related diseases, alpecia, irritable bowel syndrome, sleep disorders, epilepsy, dermatitides, schizophrenia, pain, etc.

2. Description of the Prior Art

CRF is a hormone comprising 41 amino acids (Science, 213, 1394-1397, 1981; and J. Neurosci., 7, 88-100, 1987), and it is suggested that CRF plays a core role in biological reactions against stresses (Cell. Mol. Neurobiol., 14, 579-588, 1994; Endocrinol., 132, 723-728, 1994; and Neuroendocrinol. 61, 445-452, 1995). For CRF, there are the following two paths: a path by which CRF acts on peripheral immune system or sympathetic nervous system through hypothalamus-pituitary-adrenal system, and a path by which CRF functions as a neurotransmitter in central nervous system (in Corticotropin Releasing Factor: Basic and Clinical Studies of a Neuropeptide, pp. 29-52, 1990). Intraventricular administration of CRF to hypophy-sectomized rats and normal rats causes an anxiety-like symptom in both types of rats (Pharmacol. Rev., 43, 425-473, 1991; and Brain Res. Rev., 15, 71-100, 1990). That is, there are suggested the participation of CRF in hypothalamus-pituitary-adrenal system and the pathway by which CRF functions as a neurotransmitter in central nervous system.

The review by Owens and Nemeroff in 1991 summarizes diseases in which CRF is involved (Pharmacol. Rev., 43, 425-474, 1991). That is, CRF is involved in depression, anxiety, Alzheimer's disease, Parkinson's disease, Huntington's chorea, eating disorder, hypertension, gastrointestinal diseases, drug dependence, inflammation, immunity-related diseases, etc. It has recently been reported that CRF is involved also in epilepsy, cerebral infarction, cerebral ischemia, cerebral edema, and cephalic external wound (Brain Res. 545, 339-342, 1991; Ann. Neurol. 31, 48-498, 1992; Dev. Brain Res. 91, 245-251, 1996; and Brain Res. 744, 166-170, 1997). Accordingly, antagonists against CRF receptors are useful as therapeutic agents for the diseases described above.

WO98/35967 discloses pyrrolopyrimidines or pyrrolotriazine derivatives respectively as CRF receptor antagonists. However, none disclose the compounds provided in the present invention.

Problems(s) to be Solved by Invention

An object of the present invention is to'provide an antagonist against CRF receptors which is effective as a therapeutic or prophylactic agent for diseases in which CRF is considered to be involved, such as depression, anxiety, Alzheimer's disease, Parkinson's disease, Huntington's chorea, eating disorder, hypertension, gastral diseases, drug dependence, epilepsy, cerebral infarction, cerebral ischemia, cerebral edema, cephalic external wound, inflammation, immunity-related diseases, alpecia, irritable bowel syndrome, sleep disorders, dermatitides, schizophrenia, pain, etc.

Means for Solving Problem

The present inventors earnestly investigated pyrrolopyrimidines or pyrrolotriazines substituted with a carbamoyl group that have a high affinity for CRF receptors, whereby the present invention has been accomplished.

The present invention is pyrrolopyrimidine or pyrrolotriazine derivatives substituted with a carbamoyl group explained below.

A pyrrolopyrimidine or pyrrolotriazine derivative substituted with a carbamoyl group represented by the following formula [I]:

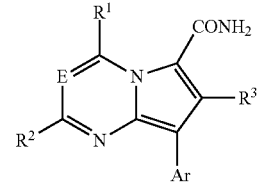

(wherein E is N or $CR^{10}$;

$R^1$ is $-OR^4$, $-S(O)_lR^4$ or $-NR^4R^5$;

$R^2$ is hydrogen, $C_{1-6}$alkyl, $C_{3-7}$cycloalkyl, $C_{3-7}$cycloalkyl-$C_{1-6}$alkyl, halogen, $C_{1-6}$alkoxy, $C_{3-7}$cycloalkyloxy, $C_{1-6}$alkylthio or $-N(R^6)R^7$;

$R^3$ is hydrogen, $C_{1-6}$alkyl, $C_{3-7}$cycloalkyl, $C_{3-7}$cycloalkyl-$C_{1-6}$alkyl or aryl;

$R^4$ and $R^5$ are the same or different, and independently hydrogen, $C_{1-9}$alkyl, $C_{3-7}$cycloalkyl, $C_{3-7}$cycloalkyl-$C_{1-6}$alkyl, di($C_{3-7}$cycloalkyl)-$C_{1-6}$alkyl, $C_{1-6}$alkoxy-$C_{1-6}$alkyl, di($C_{1-6}$alkoxy)-$C_{1-6}$alkyl, hydroxy-$C_{1-6}$alkyl, cyano-$C_{1-6}$alkyl, carbamoyl-$C_{1-6}$alkyl or di($C_{1-6}$alkyl)amino-$C_{2-6}$ alkyl; or $R^4$ and $R^5$ are taken together to form $-(CH_2)_m-A-(CH_2)_n-$ wherein A is methylene, oxygen, sulfur, $NR^8$ or $CHR^9$;

$R^6$ and $R^7$ are the same or different, and independently hydrogen or $C_{1-6}$alkyl;

$R^8$ is hydrogen, $C_{1-6}$alkyl, $C_{3-7}$cycloalkyl, aryl or aryl-$C_{1-6}$alkyl;

$R^9$ is hydrogen, hydroxy, hydroxy-$C_{1-6}$alkyl, cyano or cyano-$C_{1-6}$alkyl;

$R^{10}$ is hydrogen, halogen or $C_{1-6}$alkyl;

l is an interger selected from 0, 1 and 2;

m is an integer selected from 1, 2, 3 and 4;

n is an integer selected from 0, 1, 2 and 3;

with the proviso, when A is oxygen, sulfur or $NR^8$, then n is 1, 2 or 3;

Ar is aryl or heteroaryl which aryl or heteroaryl is unsubstituted or substituted with 1 or more substituents, which are the same or different, selected from the group consisting of halogen, $C_{1-6}$alkyl, $C_{3-7}$cycloalkyl, $C_{2-6}$alkenyl, $C_{2-6}$alkynyl, $C_{1-6}$alkoxy, $C_{1-6}$alkylthio, $C_{1-6}$alkylsulfinyl, $C_{1-6}$alkylsulfonyl, cyano, nitro, hydroxy, $-CO_2R^{11}$, $-C(=O)R^{12}$, $-CONR^{13}R^{14}$, $-OC(=O)R^{15}$, $-NR^{16}CO_2R^{17}$, $-S(=O)_rNR^{18}R^{19}$, trifluoromethyl, trifluoromethoxy, difluoromethoxy, fluoromethoxy and $-N(R^{20})R^{21}$;

$R^{11}$ and $R^{17}$ are the same or different, and independently are hydrogen, $C_{1-5}$alkyl, $C_{3-8}$cycloalkyl, $C_{3-8}$cycloalkyl-$C_{1-5}$alkyl, aryl or aryl-$C_{1-5}$alkyl;

$R^{12}$, $R^{13}$, $R^{14}$, $R^{15}$, $R^{16}$, $R^{18}$, $R^{19}$, $R^{20}$ and $R^{21}$ are the same or different, and independently are hydrogen; $C_{1-5}$alkyl or $C_{3-8}$cycloalkyl;

r is 1 or 2), individual isomers thereof or racemic or non-racemic mixtures of isomers thereof, or pharmaceutically acceptable salts and hydrates thereof.

The terms used in the present specification have the following meanings.

The term "$C_{1-9}$alkyl" means a straight chain or branched chain alkyl group of 1 to 9 carbon atoms, such as methyl, ethyl, propyl, isopropyl, butyl, isobutyl, tert-butyl, sec-butyl, pentyl, isopentyl, 1-methylbutyl, hexyl, isohexyl, 1-ethylpropyl, 1-ethylbutyl, 1,3-dimethylbutyl, 1-propylbutyl, 1-propylpentyl, 1-butylpentyl or the like.

The term "$C_{3-7}$cycloalkyl" means a cyclic alkyl, group of 3 to 7 carbon atoms, such as cyclopropyl, cyclobutyl, cyclopentyl, cyclohexyl, cycloheptyl or the like.

The term "$C_{3-7}$cycloalkyl-$C_{1-6}$alkyl" means a substituted $C_{1-6}$alkyl group having the above-mentioned $C_{3-7}$cycloalkyl as the substituent, such as cyclopropylmethyl, 1-cyclopropylethyl, 1-cyclobutylethyl, 1-cyclopentylethyl, 2-cyclopropylethyl, 2-cyclobutylethyl, 2-cyclopentylethyl, 1-cyclopropylpropyl, 1-cyclobutylpropyl, 1-cyclopentylpropyl, 1-cyclopropylmethylpropyl, 1-cyclopropylmethylbutyl or the like.

The term "$C_{3-8}$cycloalkyloxy" means a cyclic alkoxy group of 3 to 8 carbon atoms, such as cyclopropyloxy, cyclobutyloxy, cyclopentyloxy or the like.

The term "di($C_{3-7}$cycloalkyl)-$C_{1-6}$alkyl" means a substituted $C_{1-6}$alkyl group having two above-mentioned $C_{3-7}$cycloalkyl groups as the substituents, such as di(cyclopropyl)methyl, di(cyclobutyl)methyl, di(cyclopentyl)methyl or the like.

The term "$C_{1-6}$alkoxy" means a straight chain or branched chain alkoxy group of 1 to 6 carbon atoms, such as methoxy, ethoxy, propoxy, isopropyloxy, butoxy, isobutyloxy, pentyloxy, isopentyloxy or the like.

The term "$C_{1-6}$alkoxy-$C_{1-6}$alkyl" means a substituted $C_{1-6}$alkyl group having the above-mentioned $C_{1-6}$alkoxy group as the substituent, such as methoxymethyl, 2-methoxyethyl, 2-ethoxyethyl, 1-methoxymethylpropyl, 1-methoxymethylbutyl or the like.

The term "di($C_{1-6}$alkoxy)-$C_{1-6}$alkyl" means a substituted $C_{1-6}$alkyl group having two above-mentioned $C_{1-6}$alkoxy groups as the substituents, such as 2,3-di(methoxy)propyl, 2-methoxy-1-methoxymethyl-ethyl, 2,4-di(ethoxy)pentyl or the like.

The term "hydroxy-$C_{1-6}$alkyl" means a substituted $C_{1-6}$alkyl group having a hydroxy group, such as hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl, 1-hydroxymethylpropyl, 1-hydroxymethylbutyl, 1-hydroxymethyl-3-methylbutyl or the like.

The term "cyano-$C_{1-6}$alkyl" means a substituted $C_{1-6}$alkyl group having a cyano group, such as cyanomethyl, 1-cyanoethyl, 2-cyanoethyl, 1-cyanopropyl, 1-cyanobutyl, 5-cyanopentyl, 2-cyano-1-ethylethyl, 1-cyanomethylbutyl, 1-cyano-3-methylbutyl, 1-cyanomethyl-3-methyl-butyl or the like.

The term "carbamoyl-$C_{1-6}$alkyl" means a substituted $C_{1-6}$alkyl group having a carbamoyl group, such as carbamoylmethyl, 1-carbamoylethyl, 2-carbamoylethyl, 1-carbamoylpropyl, 1-carbamoylbutyl, 5-carbamoylpentyl, 1-carbamoyl-3-methylbutyl, 1-carbamoylmethylbuty, 1-carbamoylmethylpropyl, 1-carbamoylmethyl-3-methylbutyl or the like.

The term "di($C_{1-6}$alkyl)amino" means a amino group having two above-mentioned $C_{1-6}$alkyl groups, such as dimethylamino, diethylamino, dipropylamino or the like.

The term "di($C_{1-6}$alkyl)amino-$C_{2-6}$alkyl" means a substituted $C_{2-6}$alkyl group having a above-mentioned di($C_{1-6}$alkyl)amino group, such as 2-dimethylaminoethyl, 3-dimethylaminopropyl or the like.

The term "aryl" means a monocyclic or bicyclic group of 6 to 12 ring carbon atoms having at least one aromatic ring, such as phenyl, naphthyl, or the like.

The term "heteroaryl" means a monocyclic or bicyclic group of 5 to 12 ring atoms having at least one aromatic ring having in its ring 1 to 4 atoms which may be the same or different and are selected from nitrogen, oxygen and sulfur, such as pyridyl, pyrimidinyl, imidazolyl, quinolyl, indolyl, benzofuranyl, quinoxalinyl, benzo[1,2,5]thiadiazolyl, benzo[1,2,5]oxadiazolyl or the like.

The term "ary-$C_{1-5}$alkyl" means a substituted $C_{1-5}$alkyl group having the above-mentioned aryl as the substituent, such as benzyl, phenethyl or the like.

The term "halogen" means fluorine, chlorine, bromine or iodine atom.

The term "$C_{2-6}$alkenyl" means a straight chain or branched chain alkenyl group of 2 to 6 carbon atoms, such as vinyl, isopropenyl, allyl or the like.

The term "$C_{2-6}$alkynyl" means a straight chain or branched chain alkynyl group of 2 to 6 carbon atoms, such as ethynyl, prop-1-ynyl, prop-2-ynyl or the like.

The term "$C_{1-6}$alkylthio" means a straight chain or branched chain alkylthio group of 1 to 6 carbon atoms, such as methylthio, ethylthio, propylthio or the like.

The phrase "aryl or heteroaryl which aryl or heteroaryl is unsubstituted or substituted with 1 or more substituents, which are the same or different, selected from the group consisting of halogen, $C_{1-6}$alkyl, $C_{3-7}$cycloalkyl, $C_{2-6}$alkenyl, $C_{2-6}$alkynyl, $C_{1-6}$alkoxy, $C_{1-6}$alkylthio, $C_{1-6}$alkylsulfinyl, $C_{1-6}$alkylsulfonyl, cyano, nitro, hydroxy, —$CO_2R^9$, —C(=O)$R^{10}$, —CONR$^{11}$R$^{12}$, —OC(=O)$R^{13}$, —NR$^{14}$CO$_2$R$^{15}$, —S(=O)$_r$NR$^{16}$R$^{17}$, trifluoromethyl, trifluoromethoxy, difluoromethoxy, fluoromethoxy and —N(R$^{18}$)R$^{19}$" includes, for example, 2,4-dimethylphenyl, 2,6-dimethylphenyl, 2,4-dibromophenyl, 2-bromo-4-isopropylphenyl, 2,4-dichlorophenyl, 2,6-dichlorophenyl, 2-chloro-4-trifluoromethylphenyl, 4-methoxy-2-methylphenyl, 2-chloro-4-trifluoromethoxyphenyl, 4-isopropyl-2-methylthiophenyl, 2,4,6-trimethylphenyl, 4-bromo-2,6-dimethylphenyl, 4-bromo-2,6-diethylphenyl, 4-chloro-2,6-dimethylphenyl, 2,4,6-tribromophenyl, 2,4,5-tribromophenyl, 2,4,6-trichlorophenyl, 2,4,5-trichlorophenyl, 4-bromo-2,6-dichlorophenyl, 6-chloro-2,4-dibromophenyl; 2,4-dibromo-6-fluorophenyl, 2,4-dibromo-6-methylphenyl, 2,4-dibromo-6-methoxyphenyl, 2,4-dibromo-6-methylthiophenyl, 2,6-dibromo-4-isopropylphenyl, 2,6-dibromo-4-trifluoromethylphenyl, 2-bromo-4-trifluoromethylphenyl, 4-bromo-2-chlorophenyl, 2-bromo-4-chlorophenyl, 4-bromo-2-methylphenyl, 4-chloro-2-methylphenyl, 2,4-dimethoxyphenyl, 2,6-dimethyl-4-methoxyphenyl, 4-chloro-2,6-dibromophenyl, 4-bromo-2,6-difluorophenyl, 2,6-dichloro-4-trifluoromethylphenyl, 2,6-dichloro-4-trifluoromethoxyphenyl, 2,6-dibromo-4-trifluoromethoxyphenyl, 2-chloro-4,6-dimethylphenyl, 2-bromo-4,6-dimethoxyphenyl, 2-bromo-4-isopropyl-6-methoxyphenyl, 2,4-dimethoxy-6-methylphenyl, 6-dimethylamino-4-methylpyridin-3-yl, 2-chloro-6-trifluoromethyl-pyridin-3-yl, 2-chloro-6-trifluoromethoxypyridin-3-yl, 2-chloro-6-methoxypyridin-3-yl, 6-methoxy-2-trifluoromethylpyridin-3-yl, 2-chloro-6-difluoromethylpyridin-3-yl, 6-methoxy-2-methylpyridin-3-yl, 2,6-dimethoxypyridin-3-yl, 4,6-dimethyl-2-trifluoromethylpyrimidin-5-yl and 2-dimethylamino-6-methylpyridin-3-yl.

The "pharmaceutically acceptable salts" in the present invention include, for example, salts with an inorganic acid such as sulfuric acid, hydrochloric acid, hydrobromic acid, phosphoric acid, nitric acid or the like; salts with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, naphthalene-2-sulfonic acid or the like; salts with one or more metal ions such as lithium ion, sodium ion, potassium ion, calcium ion, magnesium ion, zinc ion, aluminium ion or the like; salts with an amine such as ammonia, arginine, lysine, piperazine, choline, diethylamine, 4-phenylcyclohexylamine, 2-aminoethanol, benzathine or the like.

In a compound of the present invention, isomers such as diastereomers, enantiomers, geometricisomers and tautomeric forms may exist. The compound of the present invention includes the individual isomers and the racemic and non-racemic mixtures of the isomers.

Preferable examples of the compound of the present invention are as follows.

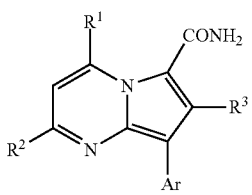

[II]

That is preferable are compounds of the formula [II] in which $R^1$, $R^2$, $R^3$ and Ar are as defined in formula [I]. More preferable are compounds of the formula [II], wherein $R^1$ is —$OR^4$ or —$NR^4R^5$; $R^2$ is $C_{1-6}$alkyl; $R^3$ is hydrogen or $C_{1-6}$alkyl; $R^4$ and $R^5$ are the same or different, and independently hydrogen, $C_{1-9}$alkyl, $C_{3-7}$cycloalkyl, $C_{3-7}$cycloalkyl-$C_{1-6}$alkyl, di($C_{3-7}$cycloalkyl)-$C_{1-6}$alkyl, $C_{1-6}$alkoxy-$C_{1-6}$alkyl, di($C_{1-6}$alkoxy)-$C_{1-6}$alkyl, hydroxy-$C_{1-6}$alkyl or cyano-$C_{1-6}$alkyl; Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl); More preferable are compounds of the formula [II], wherein $R^1$ is —$OR^4$ or —$NR^4R^5$; $R^2$ is $C_{1-6}$alkyl; $R^3$ is hydrogen or $C_{1-6}$alkyl; $R^4$ is $C_{1-9}$alkyl, $C_{3-7}$cycloalkyl, $C_{3-7}$cycloalkyl-$C_{1-6}$ alkyl, di($C_{3-7}$ cycloalkyl)-$C_{1-6}$alkyl, $C_{1-6}$alkoxy-$C_{1-6}$alkyl, di($C_{1-6}$ alkoxy)-$C_{1-6}$alkyl, hydroxy-$C_{1-6}$alkyl or cyano-$C_{1-6}$ lkyl; $R^5$ is hydrogen; Ar is phenyl which phenyl is substituted with two or three substituents, which are the same or different, selected from the group consisting of halogen and $C_{1-3}$alkyl.

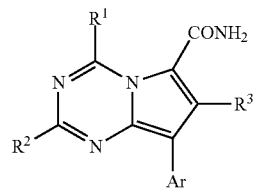

[III]

Other preferable are compounds of the formula [III] in which $R^1$, $R^2$, $R^3$ and Ar are as defined in formula [I]. More preferable are compounds of the formula [III], wherein $R^1$ is —$OR^4$ or —$NR^4R^5$; $R^2$ is $C_{1-6}$alkyl; $R^3$ is hydrogen or $C_{1-6}$alkyl; $R^4$ and $R^5$ are the same or different, and independently hydrogen, $C_{1-9}$alkyl, $C_{3-7}$cycloalkyl, $C_{3-7}$cycloalkyl-$C_{1-6}$alkyl, di($C_{3-7}$cycloalkyl)-$C_{1-6}$alkyl, $C_{1-6}$alkoxy-$C_{1-6}$alkyl, di($C_{1-6}$alkoxy)-$C_{1-6}$alkyl, hydroxy-$C_{1-6}$alkyl or cyano-$C_{1-6}$alkyl; Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl); More preferable are compounds of the formula [III], wherein $R^1$ is —$OR^4$ or —$NR^4R^5$; $R^2$ is $C_{1-6}$alkyl; $R^3$ is hydrogen or $C_{1-6}$alkyl; $R^4$ is $C_{1-9}$alkyl, $C_{3-7}$cycloalkyl, $C_{3-7}$cycloalkyl-$C_{1-6}$ alkyl, di($C_{3-7}$ cycloalkyl)-$C_{1-6}$alkyl, $C_{1-6}$alkoxy-$C_{1-6}$alkyl, di($C_{1-6}$ alkoxy)-$C_{1-6}$alkyl, hydroxy-$C_{1-6}$alkyl or cyano-$C_{1-6}$ lkyl; $R^5$ is hydrogen; Ar is phenyl which phenyl is substituted with two or three substituents, which are the same or different, selected from the group consisting of halogen and $C_{1-3}$alkyl.

The compound of the formula [I] can be produced, for example, by the process shown in the following reaction scheme 1 (in the following reaction scheme, $R^1$, $R^2$, $R^3$ and Ar are as defined above, LG is chloro, bromo, iodo, methanesulfonyloxy, benzenesulfonyloxy, toluenesulfonyloxy or trifluoromethanesulfonyloxy group, $R^a$ is $C_{1-6}$alkyl or benzyl, p is 1 or 2).

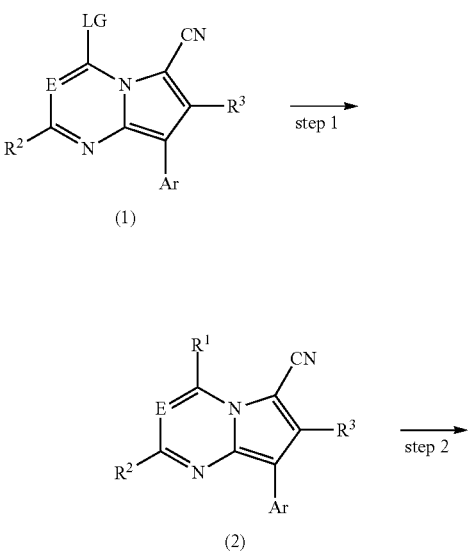

(3)

Step 1:

Compound (2) can be obtained by reacting Compound (1) with the corresponding amine in an inert solvent in the presence or absence of a base. Herein, the base includes, for example, amines such as triethylamine, N,N-diisopropylethylamine, pyridine and the like; inorganic bases such as sodium carbonate, potassium carbonate, sodium hydrogencarbonate, potassium hydrogencarbonate, potassium hydroxide, sodium hydroxide, lithium hydroxide, barium hydroxide, sodium hydride and the like; metal alcoholates such as sodium methoxide, sodium ethoxide, potassium tert-butoxide and the like; metal amides such as sodium amide, lithium diisopropylamide and the like; and Grignard reagents such as methylmagnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; esters such as ethyl acetate, ethyl formate; amides such as N,N-dimethylformamide, N-methylpyrrolidone, N,N-dimethylacetamide and the like; acetonitrile; dichloromethane; chloroform; dimethyl sulfoxide; pyridine; water; and mixtures of solvents selected from these inert solvents.

Step 2:

Conversion of a cyano group in Compound (2) into a carbamoyl group can be achieved in the presence of an acid or a base in the presence or absence of an inert solvent. When $R^1$ has a cyano group, the cyano group can be converted into a carbamoyl group at the same time. Herein, the acid includes inorganic acids such as sulfuric acid, hydrochloric acid, hydrobromic acid, phosphoric acid, polyphosphoric acid, nitric acid and the like; organic acids such as benzenesulfonic acid, toluenesulfonic acid and the like. The base includes inorganic bases such as lithium hydroxide, sodium hydroxide, potassium hydroxide, calcium hydroxide, magnesium hydroxide, zinc hydroxide, aluminium hydroxide and the like. The inert solvent includes, for example, alcohols such as methanol, ethanol, isopropyl alcohol, tert-butyl alcohol, ethylene glycol and the like; ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; acetonitrile; dichloromethane; chloroform; dimethyl sulfoxide; pyridine; water; and mixtures of solvents selected from these inert solvents.

The compound of the present invention can be converted to a salt with an acid in an inert solvent. The acid includes inorganic acids such as sulfuric acid, hydrochloric acid, hydrobromic acid, phosphoric acid, nitric acid and the like; organic acids such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, naphthalene-2-sulfonic acid and the like.

The inert solvent includes, for example, alcohols such as methanol; ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; esters such as ethyl acetate, ethyl formate and the like; ketones such as acetone, methylethylketone and the like; acetonitrile; dichloromethane; chloroform; dimethyl sulfoxide; pyridine; water; and mixtures of solvents selected from these inert solvents.

Reaction Scheme 2

(4)

(5)

(6)

(7)

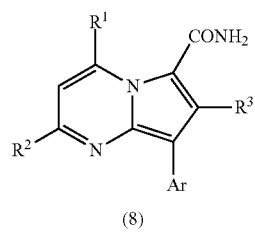

(8)

Step 3:

Conversion of Compound (4) into Compound (5) can be carried out by treatment of (4) with thiourea in an inert solvent and followed by reacting with an alkylating reagent in the presence or absence of a base in an inert solvent. Herein, the alkylating reagent includes conventional alkylating reagents such as methyl iodide, methyl bromide, dimethyl sulfate, ethyl iodide, ethyl bromide, diethyl sulfate, benzyl chloride, benzyl bromide and the like. The base includes amines such as triethylamine, N,N-diisopropylethylamine, pyridine and the like; inorganic bases such as sodium carbonate, potassium carbonate, sodium hydrogencarbonate, potassium hydrogencarbonate, potassium hydroxide, sodium hydroxide, lithium hydroxide, barium hydroxide, sodium hydride and the like; metal alcoholates such as sodium methoxide, sodium ethoxide, potassium tert-butoxide and the like; metal amides such as sodium amide, lithium diisopropylamide and the like; and Grignard reagents such as methylmagnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; amides such as N,N-dimethylformamide, N-methylpyrrolidone, N,N-dimethylacetamide and the like; acetonitrile; dichloromethane; chloroform; dimethyl sulfoxide; pyridine; water; and mixtures of solvents selected from these inert solvents.

Step 4:

Conversion of Compound (5) into Compound (6) can be achieved in the same manner as step 2.

Step 5:

Conversion of Compound (6) into Compound (7) can be carried out by reacting Compound (6) with an oxidizing reagent in an inert solvent. Herein, the oxidizing reagent includes conventional oxidizing reagents to oxidize a sulfide group such as peroxyacetic acid, hydrogen peroxide, 3-chloroperoxybenzoic acid, Oxone, sodium periodate, sodium perborate and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; amides such as N,N-dimethylformamide, N-methylpyrrolidone, N,N-dimethylacetamide and the like; acetonitrile; dichloromethane; chloroform; dimethyl sulfoxide; pyridine; water; and mixtures of solvents selected from these inert solvents.

Step 6:

Conversion of Compound (7) into Compound (8) can be carried out in the same manner as step 1.

The compound of the present invention is useful as a therapeutic or prophylactic agent for diseases in which CRF is considered to be involved. For this purpose, the compound of the present invention can be formulated into tablets, pills, capsules, granules, powders, solutions, emulsions, suspensions, injections and the like by a conventional preparation technique by adding conventional fillers, binders, disintegrators, pH-adjusting agents, solvents, etc.

The compound of the present invention can be administered to an adult patient in a dose of 0.1 to 500 mg per day in one portion or several portions orally or parenterally. The dose can be properly increased or decreased depending on the kind of a disease and the age, body weight and symptom of a patient.

EMBODIMENTS OF THE INVENTION

The present invention is concretely explained with reference to the following examples and test example, but is not limited thereto.

EXAMPLE 1

Synthesis of 8-(4-bromo-2,6-dimethyl-phenyl)-2-methyl-4-(1-propyl-butylamino)-pyrrolo[1,2-a]pyrimidine-6-carboxylic acid amide hydrochloride (Compound 1-001)

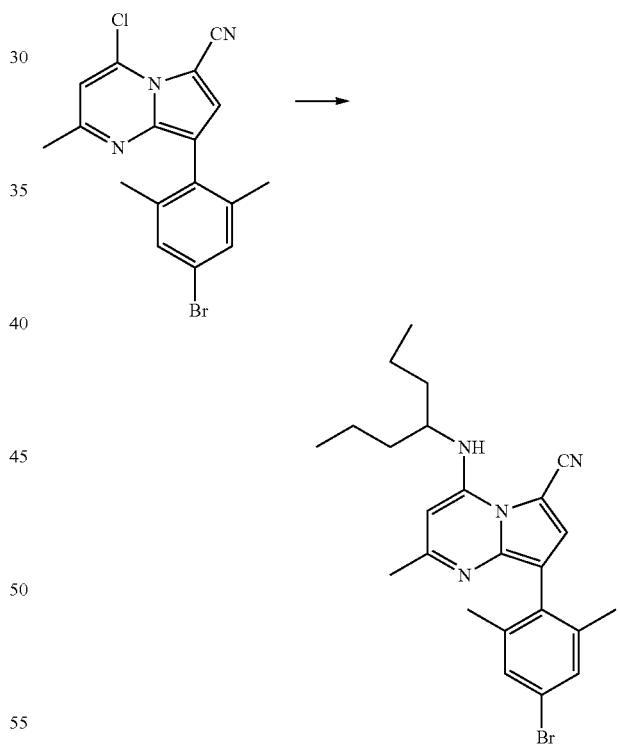

(1) A mixture of 8-(4-bromo-2,6-dimethyl-phenyl)-4-chloro-2-methyl-pyrrolo[1,2-a]pyrimidine-6-carbonitrile (30.0 g), 1-propyl-butylamine (18.5 g), N,N-diisopropylethylamine (15.5 g) in ethanol (90 mL) was heated at reflux for 2 h. The reaction mixture was cooled to room temperature, poured into a saturated aqueous sodium hydrogencarbonate, and then extracted with ethyl acetate. The organic layer was washed with brine, dried over anhydrous sodium sulfate and filtered. The filtrate was concentrated under reduced pressure to give a solid. The solid was washed with diisopropylether to give 8-(4-bromo-2,6-dimethyl-phenyl)-2-methyl-4-(1-propyl-butylamino)-pyrrolo[1,2-a]pyrimidine-6-carbonitrile (27.0 g).

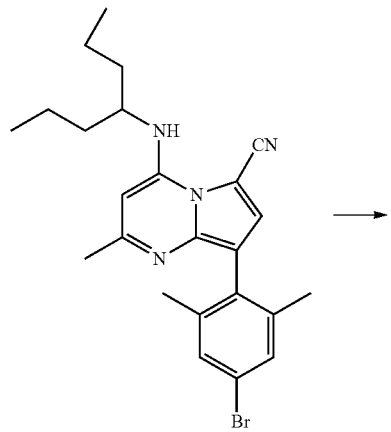

(2) 8-(4-Bromo-2,6-dimethyl-phenyl)-2-methyl-4-(1-propyl-butylamino)-pyrrolo[1,2-a]pyrimidine-6-carbonitrile (10.0 g) was added into conc. $H_2SO_4$ (50 mL) and heated for 55° C. for 5 hours. The reaction mixture was cooled to room temperature, poured into ice-water and then a saturated aqueous sodium hydrogencarbonate was added to make the aqueous mixture alkaline (pH=8) and extracted with ethyl acetate. The organic layer was washed with brine, dried over anhydrous sodium sulfate and filtered. The filtrate was concentrated under reduced pressure and the residue was purified by a silica gel column chromatography (silica gel: Wako Gel (C200), eluent: hexane/ethyl acetate/chloroform=10:3:1) to give a solid. The solid was recrystallized from ethyl acetate to provide 8-(4-bromo-2,6-dimethyl-phenyl)-2-methyl-4-(1-propyl-butylamino)-pyrrolo[1,2-a]pyrimidine-6-carboxylic acid amide (5.8 g).

(3) To a suspension of 8-(4-bromo-2,6-dimethyl-phenyl)-2-methyl-4-(1-propyl-butylamino)-pyrrolo[1,2-a]pyrimidine-6-carboxylic acid amide (5.8 g) in ethanol (30 mL) was added 4 M HCl/ethyl acetate (3.7 mL) in an ice-cooling bath. The resulting solution was concentrated under reduced pressure. The residue was crystallized from ethyl acetate to give the title compound.

Table 1 and table 2 list the compound obtained in Example 1 and compounds obtained by the similar procedure as described in Example 1.

EXAMPLE 2

Synthesis of 8-(4-bromo-2,6-dimethyl-phenyl)-2-methyl-4-(N,N-dipropylamino)-pyrrolo[1,2-a]pyrimidine-6-carboxylic acid amide (Compound 1-022)

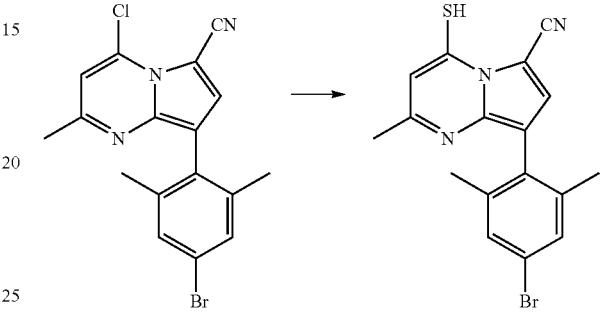

(1) A mixture of 8-(4-bromo-2,6-dimethyl-phenyl)-4-chloro-2-methyl-pyrrolo[1,2-a]pyrimidine-6-carbonitrile (7.50 g), thiourea (7.11 g) in ethanol (50 mL) was heated at reflux for 2 h. The reaction mixture was cooled to room temperature, poured into 0.5 M NaOH aqueous solution, stirred for 1 hour and extracted with ethyl acetate. The organic layer was washed with brine, dried over anhydrous sodium sulfate and filtered. The filtrate was concentrated under reduced pressure and the residue was purified by a silica gel column chromatography (silica gel: Wako Gel (C200), eluent: chloroform/methanol=10:1) to give 8-(4-bromo-2,6-dimethyl-phenyl)-4-mercapto-2-methyl-pyrrolo[1,2-a]pyrimidine-6-carbonitrile (7.52 g).

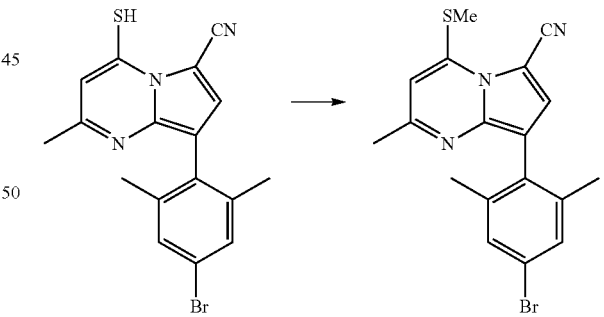

(2) A mixture of 8-(4-bromo-2,6-dimethyl-phenyl)-4-mercapto-2-methyl-pyrrolo[1,2-a]pyrimidine-6-carbonitrile (7.50 g), MeI (12.5 mL) in 1 M NaOH aqueous solution (100 mL) was stirred at room temperature for 1 h. The reaction mixture was extracted with ethyl acetate. The organic layer was washed with brine, dried over anhydrous sodium sulfate and filtered. The filtrate was concentrated under reduced pressure to give crude 8-(4-bromo-2,6-dimethyl-phenyl)-2-methyl-4-methylsulfanyl-pyrrolo[1,2-a]pyrimidine-6-carbonitrile (5.75 g). This product was used in the next step without further purification.

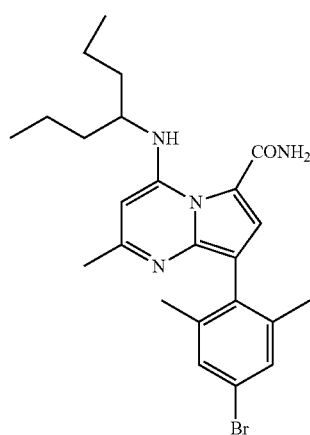

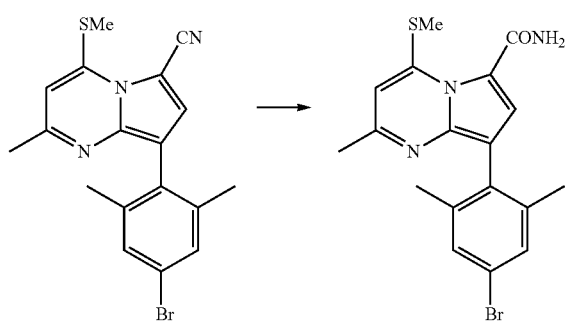

(3) 8-(4-bromo-2,6-dimethyl-phenyl)-2-methyl-4-methylsulfanyl-pyrrolo[1,2-a]pyrimidine-6-carbonitrile (5.70 g) was added into conc. $H_2SO_4$ (100 mL) and heated for 60° C. for 5 hours. The reaction mixture was cooled to room temperature, poured into ice-water and then 10% aqueous NaOH solution was added to make the aqueous mixture alkaline (pH=8) and extracted with ethyl acetate. The organic layer was washed with brine, dried over anhydrous sodium sulfate and filtered. The filtrate was concentrated under reduced pressure and the residue was purified by a silica gel column chromatography (silica gel: Wako Gel (C200), eluent: ethyl acetate) to give 8-(4-bromo-2,6-dimethyl-phenyl)-2-methyl-4-methylsulfanyl-pyrrolo[1,2-a]pyrimidine-6-carboxylic acid amide (3.12 g).

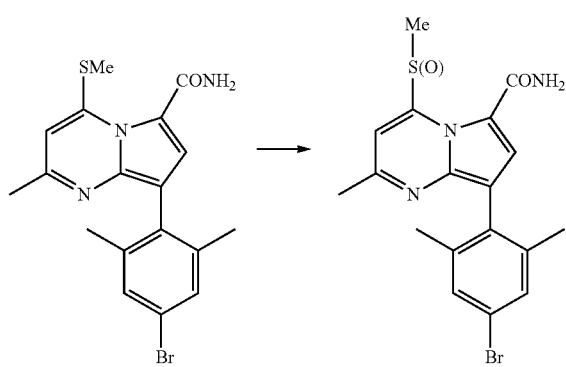

(4) To a solution of Oxone (9.12 g) in water (50 mL) was added a solution of 8-(4-bromo-2,6-dimethyl-phenyl)-2-methyl-4-methylsulfanyl-pyrrolo[1,2-a]pyrimidine-6-carboxylic acid amide (3.00 g) in ethanol (50 mL) in an ice-cooling bath. The reaction mixture was stirred under ice-cooling for 30 minutes, poured into water and extracted with ethyl acetate. The organic layer was washed with a saturated aqueous sodium hydrogencarbonate and brine, dried over anhydrous sodium sulfate and filtered. The filtrate was concentrated under reduced pressure and the residue was purified by a silica gel column chromatography (silica gel: Wako Gel (C200), eluent: ethyl acetate) to give 8-(4-bromo-2,6-dimethyl-phenyl)-4-methanesulfinyl-2-methyl-pyrrolo[1,2-a]pyrimidine-6-carboxylic acid amide (1:68 g).

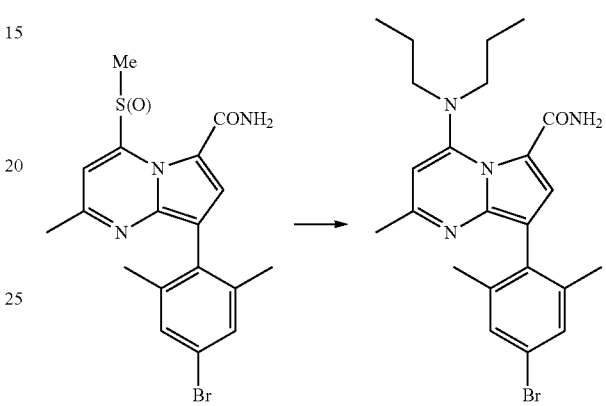

(5) A mixture of 8-(4-bromo-2,6-dimethyl-phenyl)-4-methanesulfinyl-2-methyl-pyrrolo[1,2-a]pyrimidine-6-carboxylic acid amide (100 mg), N,N-dipropylamine (48 mg) in ethanol (1 mL) was heated at reflux for 1 h. The reaction mixture was cooled to room temperature, poured into a saturated aqueous sodium hydrogencarbonate, and then extracted with ethyl acetate. The organic layer was washed with brine, dried over anhydrous sodium sulfate and filtered. The filtrate was concentrated under reduced pressure and the residue was purified by a silica gel column chromatography (silica gel: Wako Gel (C200), eluent: hexane/ethyl acetate=1:1) to give a solid. The solid was washed with a mixture of diisopropylether and ethyl acetate to give the title compound (50 mg).

Table 1 lists the compound obtained in Example 2 and compounds obtained by the similar procedure as described in Example 2.

TABLE 1[*1]

| Com. No. | Ex. No. | $R^1$ | $R^2$ | $R^3$ | Ar | melting point (° C.) (solvent for crystallization) |
|---|---|---|---|---|---|---|
| 1-001 | 1 | (sec-pentyl-NH-) | $CH_3$ | H | (4-bromo-2,6-dimethylphenyl) | 163-165[*2] (EtOAc/EtOH) |

TABLE 1*1-continued
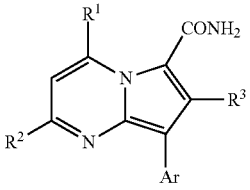
| Com. No. | Ex. No. | R¹ | R² | R³ | Ar | melting point (° C.) (solvent for crystallization) |
|---|---|---|---|---|---|---|
| 1-002 | 1 | 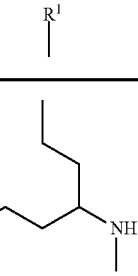 | CH₃ | H | 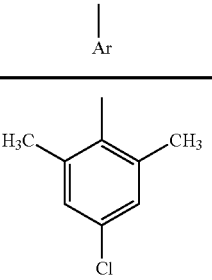 | 195-197*2 (EtOAc/EtOH) |
| 1-003 | 1 | 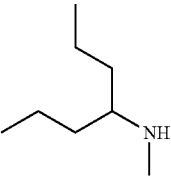 | CH₃ | H | 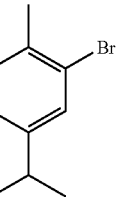 | 213-215*2 (EtOAc/EtOH) |
| 1-004 | 1 | 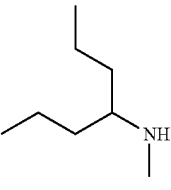 | CH₃ | H | 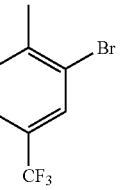 | 204-206*2 (EtOAc/EtOH) |
| 1-005 | 1 | 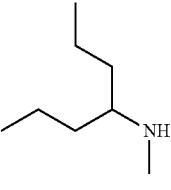 | CH₃ | H | 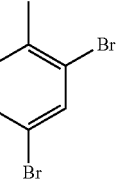 | 203-205*2 (EtOAc/EtOH) |
| 1-006 | 1 | 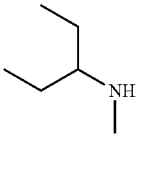 | CH₃ | H | 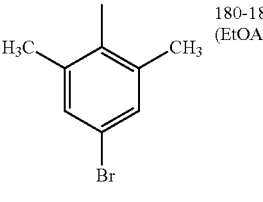 | 180-182*2 (EtOAc/EtOH) |
| 1-007 | 1 | 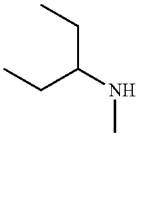 | CH₃ | H | 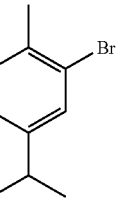 | 166-168*2 (EtOAc/EtOH) |

TABLE 1*1-continued
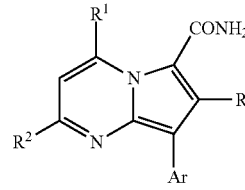
| Com. No. | Ex. No. | R¹ | R² | R³ | Ar | melting point (° C.) (solvent for crystallization) |
|---|---|---|---|---|---|---|
| 1-008 | 1 | 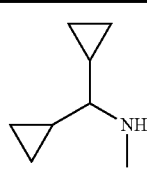 | CH₃ | H | 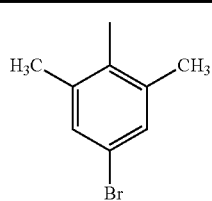 | 175-177*² (EtOAc/EtOH) |
| 1-009 | 1 | 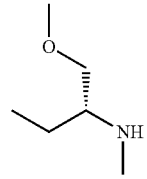 | CH₃ | H | 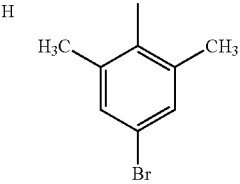 | 172-174*² (EtOAc/EtOH) |
| 1-010 | 1 | 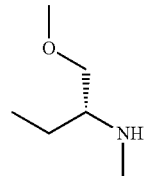 | CH₃ | H | 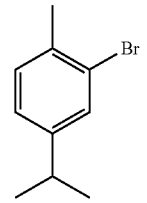 | 160-162*² (EtOAc/EtOH) |
| 1-011 | 1 | 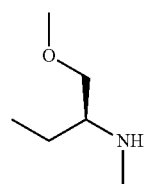 | CH₃ | H | 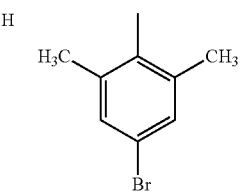 | 172-174*² (EtOAc/EtOH) |
| 1-012 | 1 | 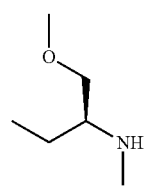 | CH₃ | H | 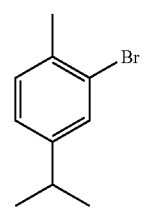 | 166-168*² (EtOAc/EtOH) |
| 1-013 | 1 | 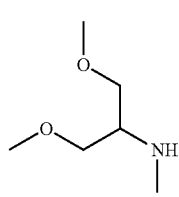 | CH₃ | H | 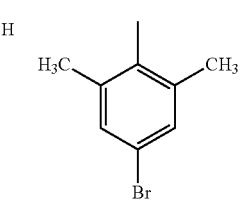 | 203-205*² (EtOAc/EtOH) |

TABLE 1*1-continued
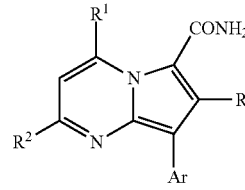
| Com. No. | Ex. No. | R1 | R2 | R3 | Ar | melting point (° C.) (solvent for crystallization) |
|---|---|---|---|---|---|---|
| 1-014 | 1 | 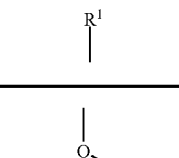 | CH3 | H | 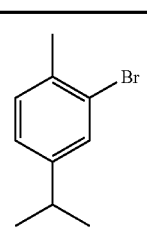 | 188-190*2 (EtOAc/EtOH) |
| 1-015 | 1 | 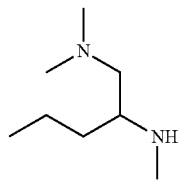 | CH3 | H | 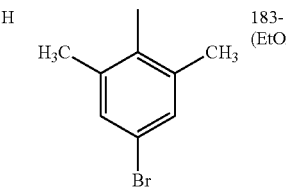 | 183-185*2 (EtOAc) |
| 1-016 | 1 | 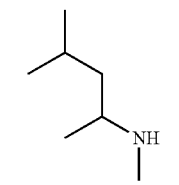 | CH3 | H | 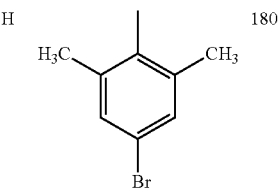 | 180-182*2*3 |
| 1-017 | 1 | 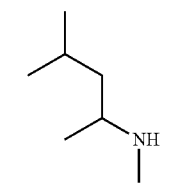 | CH3 | H | 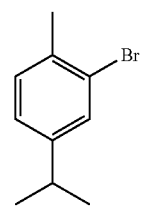 | 163-165*2*3 |
| 1-018 | 2 | 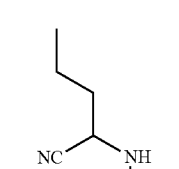 | CH3 | H | 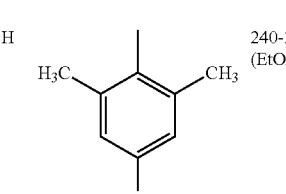 | 240-242 (EtOAc) |
| 1-019 | 2 | 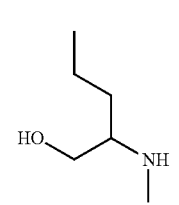 | CH3 | H | 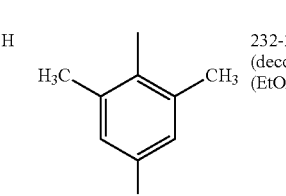 | 232-234 (decomp.) (EtOAc) |

TABLE 1*1-continued
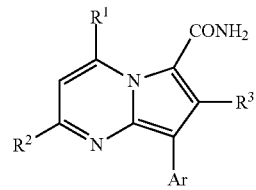
| Com. No. | Ex. No. | R1 | R2 | R3 | Ar | melting point (° C.) (solvent for crystallization) |
|---|---|---|---|---|---|---|
| 1-020 | 2 | 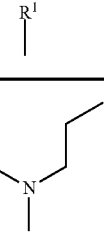 | CH3 | H | 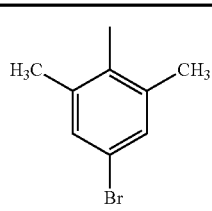 | 199-201 (EtOAc) |
| 1-021 | 2 | 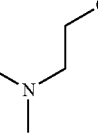 | CH3 | H | 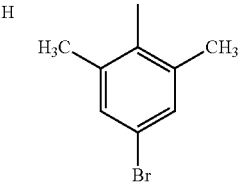 | 208-210 (EtOAc) |
| 1-022 | 2 | 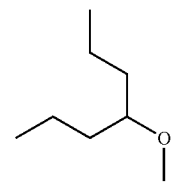 | CH3 | H | 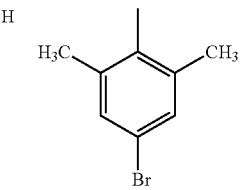 | 178-180 (EtOAc) |
| 1-023 | 2 |  | CH3 | H | 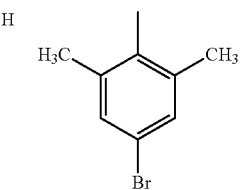 | 194-196*3 |
| 1-024 | 2 |  | CH3 | H | 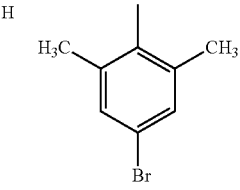 | amorphous |
| 1-025 | 2 | 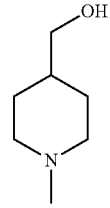 | CH3 | H | 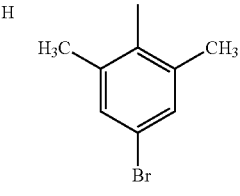 | 223-225 (EtOAc) |

TABLE 1*1-continued

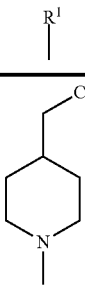

| Com. No. | Ex. No. | R¹ | R² | R³ | Ar | melting point (° C.) (solvent for crystallization) |
|---|---|---|---|---|---|---|
| 1-026 | 2 | 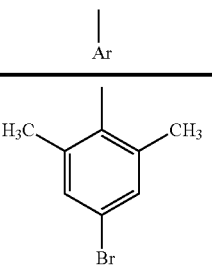 | CH₃ | H | 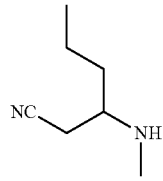 | 227-229 (EtOAc) |
| 1-027 | 2 | 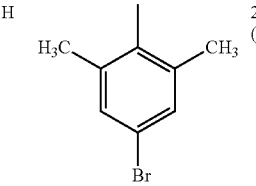 | CH₃ | H | 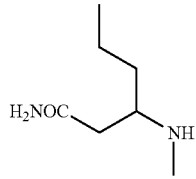 | 222-224 (EtOAc) |
| 1-028 | 1 | 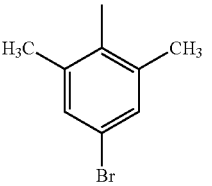 | CH₃ | H | 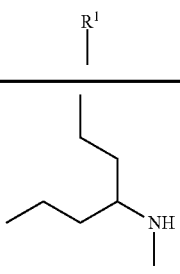 | amorphous |

*¹Com. No. = compound number, Ex. No. = example number, solvent for crystallization; EtOAc = ethyl acetate, EtOH = ethanol
Analytical data of non-crystal compounds are described below.
1-024: MS (Pos, ES): 442 (M + Na)⁺, 444 (M + Na + 2)⁺; NMR (300 MHz, CDCl₃) δ 2.04 (3 H, s), 2.09 (3 H, s), 2.58 (3 H, s), 3.17 (3 H, s), 5.54-5.66 (2 H, m), 7.26 (1 H, s), 7.31 (2 H, s), 7.59 (1 H, s)
1-028: MS (Pos, ES): 486 (M + 1)⁺, 488 (M + 3)⁺, 508 (M + Na)⁺, 510 (M + Na + 2)⁺; NMR (300 MHz, CDCl₃) δ 0.98 (3 H, t, J = 7.3 Hz), 1.40-1.64 (2 H, m), 1.68-1.79 (2 H, m), 2.09 (3 H, s), 2.10 (3 H, s), 2.37 (3 H, s), 2.51 (1 H, dd, J = 5.9, 14.4 Hz), 2.65 (1 H, dd, J = 7.4, 14.4 Hz), 4.07-4.18 (1 H, m), 5.28-5.39 (1 H, br s), 5.48-5.58 (2 H, br s), 5.72-5.87 (1 H, br s), 5.89 (1 H, s), 7.22 (1 H, s), 7.26 (3 H, s), 10.75-10.92 (1 H, br s)
*²HCl salt (Compound 1-015 is 2HCl salt)
*³Crystallized on standing from the compound purified (silica gel column chromatography) and dried.

TABLE 2*1

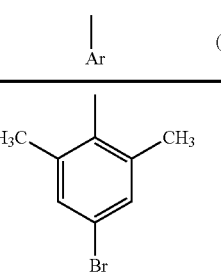

| Com. No. | Ex. No. | R¹ | R² | R³ | Ar | melting point (° C.) (solvent for crystallization) |
|---|---|---|---|---|---|---|
| 2-001 | 1 | (structure) | CH₃ | H | (structure) | 225-227*² (EtOAc/IPE) |

TABLE 2*¹-continued

General structure: pyrrolo-triazine core with $R^1$, $R^2$, $R^3$, Ar substituents and $CONH_2$ group.

| Com. No. | Ex. No. | $R^1$ | $R^2$ | $R^3$ | Ar | melting point (° C.) (solvent for crystallization) |
|---|---|---|---|---|---|---|
| 2-002 | 1 | CH₃CH₂CH(Et)-N(CH₃)- (pentan-3-yl methylamino) | CH₃ | H | 4-Br-3,5-dimethylphenyl | 244-246*² (EtOAc) |
| 2-003 | 1 | dicyclopropylmethyl-N(CH₃)- | CH₃ | H | 4-Br-3,5-dimethylphenyl | 229-231*² (EtOAc) |
| 2-004 | 1 | (S)-1-methoxymethyl-propyl-N(CH₃)- | CH₃ | H | 4-Br-3,5-dimethylphenyl | 214-216*² (EtOAc) |
| 2-005 | 1 | (R)-1-methoxymethyl-propyl-N(CH₃)- | CH₃ | H | 4-Br-3,5-dimethylphenyl | 218-220*² (EtOAc) |
| 2-006 | 1 | 1,3-dimethoxypropan-2-yl-N(CH₃)- | CH₃ | H | 4-Br-3,5-dimethylphenyl | 206-208*² (decomp.) (EtOAc) |

*¹Com. No. = compound number, Ex. No. = example number, solvent for crystallization; EtOAc = ethyl acetate, IPE = diisopropylether
*²HCl salt Test Example [CRF Receptor Binding Test]

Monkey amygdala membranes were used as a receptor preparation.

$^{125}$I-CRF was used as $^{125}$I-labeled ligand.

Binding reaction using the $^{125}$I-labeled ligand was carried out by the following method described in The Journal of Neuroscience, 7, 88 (1987).

Preparation of receptor membranes:

Monkey amygdala was homogenized in 50 mM Tris-HCl buffer (pH 7.0) containing 10 mM MgCl₂, 2 mM EDTA and centrifuged at 48,000×g for 20 min, and the precipitate was washed once with Tris-HCl buffer. The washed precipitate was suspended in 50 mM Tris-HCl buffer (pH 7.0) containing 10 mM MgCl₂, 2 mM EDTA, 0.1% bovine serum albumin and 100 kallikrein units/ml aprotinin, to obtain a membrane preparation.

CRF receptor binding test:

The membrane preparation (0.3 mg protein/ml), $^{125}$I-CRF (0.2 nM) and a test drug were reacted at 25° C. for 2 hours. After completion of the reaction, the reaction mixture was filtered by suction through a glass filter (GF/C) treated with 0.3% polyethylene imine, and the glass filter was washed three times with phosphate-buffered saline containing 0.01%

Triton X-100. After the washing, the radioactivity of the filter paper was measured in a gamma counter.

The amount of $^{125}$I-CRF bound when the reaction was carried out in the presence of 1 µM CRF was taken as the degree of nonspecific binding of $^{125}$I-CRF, and the difference between the total degree of $^{125}$I-CRF binding and the degree of nonspecific $^{125}$I-CRF binding was taken as the degree of specific $^{125}$I-CRF binding. An inhibition curve was obtained by reacting a definite concentration (0.2 nM) of $^{125}$I-CRF with various concentrations of each test drug under the conditions described above. A concentration of the test drug at which binding of $^{125}$I-CRF is inhibited by 50% (IC$_{50}$) was determined from the inhibition curve.

As a result, it was found that compounds 1-001, 1-002, 1-003, 1-004, 1-005, 1-006, 1-007, 1-008, 1-009, 1-010, 1-011, 1-012, 1-013, 1-016, 1-017, 1-018, 1-019, 1-022, 1-027, 2-001, 2-002, 2-003, 2-004, 2-005 and 2-006 can be exemplified as typical compounds having an IC$_{50}$ value of 100 nM or less.

EFFECT OF THE INVENTION

According to the present invention, compounds having a high affinity for CRF receptors have been provided. These compounds are effective against diseases in which CRF is considered to be involved, such as depression, anxiety, Alzheimer's disease, Parkinson's disease, Huntington's chorea, eating disorder, hypertension, gastral diseases, drug dependence, epilepsy, cerebral infarction, cerebral ischemia, cerebral edema, cephalic external wound, inflammation, immunity-related diseases, alpecia, irritable bowel syndrome, sleep disorders, dermatitides, schizophrenia, pain, etc.

The invention claimed is:

1. A compound represented by the following formula [I]:

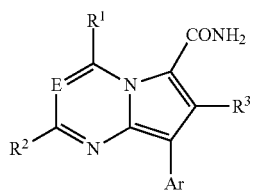

[I]

(wherein E is N or CR$^{10}$;
R$^1$ is —OR$^4$, —S(O)$_l$R$^4$ or —NR$^4$R$^5$;
R$^2$ is C$_{1-6}$alkyl;
R$^3$ is hydrogen;
R$^4$ and R$^5$ are the same or different, and independently hydrogen, C$_{1-9}$alkyl, C$_{3-7}$cycloalkyl, C$_{3-7}$cycloalkyl-C$_{1-6}$ alkyl, di(C$_{3-7}$cycloalkyl)-C$_{1-6}$alkyl, C$_{1-6}$alkoxy-C$_{1-6}$ alkyl, di(C$_{1-6}$alkoxy)-C$_{1-6}$alkyl, hydroxy-C$_{1-6}$ alkyl, cyano-C$_{1-6}$alkyl, carbamoyl-C$_{1-6}$alkyl or di(C$_{1-6}$ alkyl)amino-C$_{2-6}$alkyl; or R$^4$ and R$^5$ are taken together to form —(CH$_2$)$_m$-A-(CH$_2$)$_n$— wherein A is CHR$^9$;
R$^9$ is hydrogen, hydroxy, hydroxy-C$_{1-6}$alkyl, cyano or cyano-C$_{1-6}$alkyl;
R$^{10}$ is hydrogen;
l is an integer selected from 0, 1 and 2;
m is an integer selected from 1, 2, 3 and 4;
n is an integer selected from 0, 1, 2 and 3;
Ar is phenyl which phenyl is substituted with 1 or more substituents, which are the same or different, selected from the group consisting of halogen, C$_{1-6}$alkyl, and trifluoromethyl;
or pharmaceutically acceptable salts thereof.

2. The compound according to claim 1 represented by the following formula [II]:

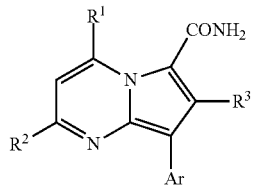

[II]

wherein R$^1$, R$^2$, R$^3$ and Ar are as defined in claim 1 or pharmaceutically acceptable salts thereof.

3. The compound according to claim 2 represented by the formula [II], wherein R$^1$ is —OR$^4$ or —NR$^4$R$^5$; R$^4$ and R$^5$ are the same or different, and independently hydrogen, C$_{1-9}$alkyl, C$_{3-7}$cycloalkyl, C$_{3-7}$cycloalkyl-C$_{1-6}$alkyl, di(C$_{3-7}$cycloalkyl)-C$_{1-6}$alkyl, C$_{1-6}$alkoxy-C$_{1-6}$alkyl, di(C$_{1-6}$lkoxy)-C$_{1-6}$ alkyl, hydroxy-C$_{1-6}$alkyl or cyano-C$_{1-6}$alkyl; Ar is phenyl which phenyl is substituted with two or three substituents, which are the same or different, selected from the group consisting of halogen, C$_{1-3}$alkyl, and trifluoromethyl, or pharmaceutically acceptable salts thereof.

4. The compound according to claim 2 represented by the formula [II], wherein R$^1$ is —OR$^4$ or —NR$^4$R$^5$; R$^4$ is C$_{1-9}$alkyl, C$_{3-7}$cycloalkyl, C$_{3-7}$cycloalkyl-C$_{1-6}$alkyl, di(C$_{3-7}$cycloalkyl)-C$_{1-6}$alkyl, di(C$_{1-6}$alkoxy) -C$_{1-6}$alkyl, hydroxy-C$_{1-6}$alkyl or cyano-C$_{1-6}$alkyl; R$^5$ is hydrogen; Ar is phenyl which phenyl is substituted with two or three substituents, which are the same or different, selected from the group consisting of halogen and C$_{1-3}$alkyl, or pharmaceutically acceptable salts thereof.

5. The compound according to claim 1 represented by the following formula [III]:

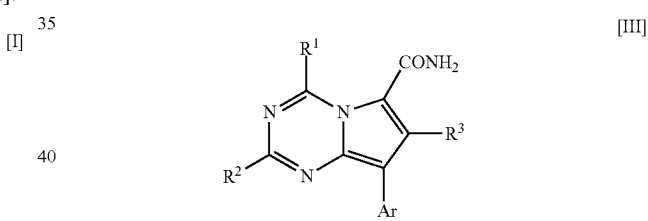

[III]

wherein R$^1$, R$^2$, R$^3$ and Ar are as defined in claim 1, or pharmaceutically acceptable salts thereof.

6. The compound according to claim 5 represented by the formula [III], wherein R$^1$ is —OR$^4$ or —NR$^4$R$^5$; R$^4$ and R$^5$ are the same or different, and independently hydrogen, C$_{1-9}$alkyl, C$_{3-7}$cycloalkyl, C$_{3-7}$cycloalkyl-C$_{1-6}$alkyl, di(C$_{3-7}$ cycloalkyl)-C$_{1-6}$alkyl, C$_{1-6}$alkoxy-C$_{1-6}$alkyl, di(C$_{1-6}$ alkoxy)-C$_{1-6}$alkyl, hydroxy-C$_{1-6}$alkyl or cyano-C$_{1-6}$alkyl; Ar is phenyl which phenyl is substituted with two or three substituents, which are the same or different, selected from the group consisting of halogen and C$_{1-3}$alkyl, or pharmaceutically acceptable salts thereof.

7. The compound according to claim 5 represented by the formula [III], wherein R$^1$ is —OR$^4$ or —NR$^4$R$^5$; R$^4$ is C$_{1-9}$alkyl, C$_{3-7}$cycloalkyl, C$_{3-7}$cycloalkyl-C$_{1-6}$alkyl, di(C$_{3-7}$ cycloalkyl)-C$_{1-6}$alkyl, C$_{1-6}$alkoxy-C$_{1-6}$alkyl, di(C$_{1-6}$ alkoxy)-C$_{1-6}$alkyl, hydroxy-C$_{1-6}$alkyl or cyano-C$_{1-6}$alkyl; R$^5$ is hydrogen; Ar is phenyl which phenyl is substituted with two or three substituents, which are the same or different, selected from the group consisting of halogen and C$_{1-3}$alkyl, or pharmaceutically acceptable salts thereof.

* * * * *